United States Patent
Legland et al.

(10) Patent No.: US 11,547,658 B2
(45) Date of Patent: Jan. 10, 2023

(54) METHOD FOR DYEING OR MAKING UP EYEBROWS

(71) Applicant: L V M H RECHERCHE, Saint-Jean de Brave (FR)

(72) Inventors: Lorraine Legland, Orleans (FR); Patrick Choisy, Montilouis sur Loire (FR); Virginie Pecher, La Chapelle Saint Mesmin (FR)

(73) Assignee: L V M H RECHERCHE, Saint-Jean de Brave (FR)

( * ) Notice: Subject to any disclaimer, the term of this patent is extended or adjusted under 35 U.S.C. 154(b) by 0 days.

(21) Appl. No.: 17/415,996

(22) PCT Filed: Dec. 18, 2019

(86) PCT No.: PCT/EP2019/085862
§ 371 (c)(1),
(2) Date: Jun. 18, 2021

(87) PCT Pub. No.: WO2020/127431
PCT Pub. Date: Jun. 25, 2020

(65) Prior Publication Data
US 2021/0378946 A1    Dec. 9, 2021

(30) Foreign Application Priority Data
Dec. 20, 2018 (FR) ...................... 1873629

(51) Int. Cl.
*A61K 8/00* (2006.01)
*A61K 8/9789* (2017.01)
(Continued)

(52) U.S. Cl.
CPC .............. *A61K 8/9789* (2017.08); *A61K 8/19* (2013.01); *A61K 8/23* (2013.01); *A61K 8/4973* (2013.01);
(Continued)

(58) Field of Classification Search
CPC . A61Q 5/065; A61Q 5/10; A61Q 1/02; A61K 8/19; A61K 2800/4322;
(Continued)

(56) References Cited

U.S. PATENT DOCUMENTS 8,313,537 B2 * 11/2012 Xue .................... A61K 8/447
8/405
2009/0249563 A1  10/2009 Greaves et al.
(Continued)

FOREIGN PATENT DOCUMENTS

EP            2399567 A1   12/2011
WO   WO-2014/029843 A1    2/2014
WO   WO-2014/106604 A1    7/2014

OTHER PUBLICATIONS

International Search Report and Written Opinion for corresponding International Application No. PCT/EP2019/085862, dated Jun. 23, 2020.
(Continued)

*Primary Examiner* — Eisa B Elhilo
(74) *Attorney, Agent, or Firm* — Marshall, Gerstein & Borun LLP

(57) ABSTRACT

The present invention concerns a cosmetic method for dyeing or making up keratin fibres, in particular eyelashes and/or eyebrows and preferably eyebrows, comprising the application, to the keratin fibres, of at least: a) A dyeing cosmetic composition A comprising, in a physiologically acceptable medium, one or more natural dye(s) chosen from the group consisting of neoflavonoids, gallic tannins and catechic tannins, and/or proanthocyanidins and the derivatives of same and the mixtures thereof, or preferably one or more plant extracts containing same, and advantageously an antioxidant, b) A revealing cosmetic composition B comprising, in a physiologically acceptable medium, at least one iron salt and/or one aluminium salt, in particular an iron
(Continued)

gluconate or an iron sulphate, composition A being applied before or after composition B, and preferably before composition B.

4 Claims, 1 Drawing Sheet

(51) Int. Cl.
*A61K 8/19* (2006.01)
*A61K 8/23* (2006.01)
*A61K 8/49* (2006.01)
*A61K 8/60* (2006.01)
*A61K 8/81* (2006.01)
*A61Q 5/06* (2006.01)

(52) U.S. Cl.
CPC ............ *A61K 8/602* (2013.01); *A61K 8/8147* (2013.01); *A61Q 5/065* (2013.01); *A61K 2800/432* (2013.01); *A61K 2800/4322* (2013.01); *A61K 2800/884* (2013.01)

(58) Field of Classification Search
CPC .......... A61K 2800/43; A61K 2800/432; A61K 2800/884; A61K 8/9789; A61K 8/26; A61K 8/922; A61K 8/602
USPC ............................................................ 8/405
See application file for complete search history.

(56) References Cited

U.S. PATENT DOCUMENTS

| | | | |
|---|---|---|---|
| 2010/0092409 A1* | 4/2010 | Amin .................. | A61K 8/64 424/59 |
| 2012/0014885 A1* | 1/2012 | Collier ................ | A61Q 9/00 424/59 |
| 2017/0151164 A1* | 6/2017 | Scheunemann ........ | A61K 8/42 |

OTHER PUBLICATIONS

Mintel., "All Natural Pemanent Hair Color" Apr. 26, 2011. Extract from www.gnpd.com, Database accession No. 1522982.
Preliminary Search Report issued for French Application No. 1873629, dated Oct. 24, 2019.

* cited by examiner

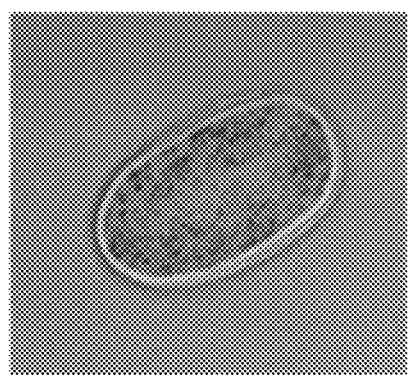
1a
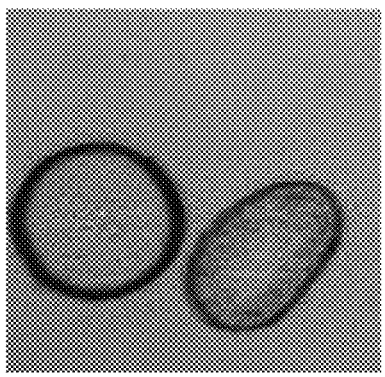 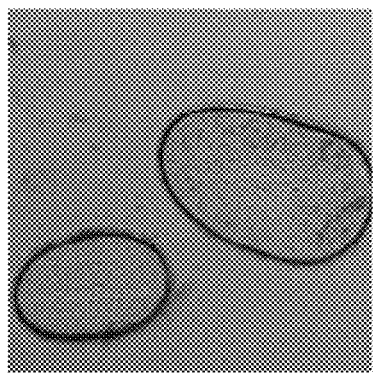 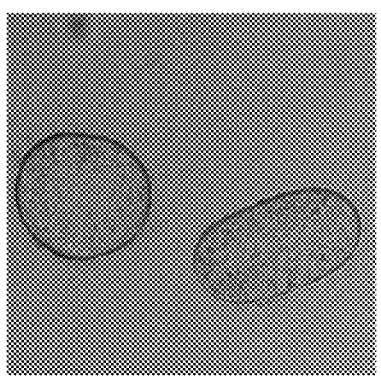
1b　　　　　　　　　1c　　　　　　　　　1d

METHOD FOR DYEING OR MAKING UP EYEBROWS

CROSS-REFERENCE TO RELATED APPLICATIONS

This application is a U.S. National Stage of International Patent Application No. PCT/EP2019/085862 filed Dec. 18, 2019, which claims the benefit of priority of French Patent Application No. 1873629 filed Dec. 20, 2018, the respective disclosures of which are each incorporated herein by reference in their entireties.

FIELD OF THE INVENTION

The present invention concerns the field of dyeing or making up keratin fibres, in particular eyelashes and/or eyebrows and, preferably, eyebrows.

STATE OF THE ART

Compositions are known from the prior art for dyeing or making up keratin materials, in particular the skin or hair, comprising natural dyes, in particular plant extracts containing polyphenols. Dye methods using natural products, more respectful of the nature of the fibres and the environment, are increasingly appreciated by users.

However, the dye or makeup result, in particular when it is a case of keratin fibres, is not always satisfactory in terms of intensity and/or homogeneity and/or longevity.

There is therefore a need to develop new compositions and methods for dyeing or making up keratin fibres, in particular the eyelashes and/or eyebrows and preferably eyebrows, comprising natural dyes based on polyphenols, with improved chromatic properties (intensity and homogeneity of colour) and that are resistant to washing, perspiration and/or sebum.

The Applicant has, rightly, discovered that it was possible to improve the efficacy of compositions for dyeing or making up keratin fibres, in particular eyebrows, by using particular plant extracts and iron salts and/or aluminum salts, in particular iron gluconate. They have especially demonstrated that the use of specific penetration booster agents makes it possible to improve the intensity and longevity of the colour.

The Applicant has also demonstrated, for dye or makeup compositions in the form of gels comprising iron gluconate, that the use of a particular acrylate copolymer was advantageous for the stability and texture of the compositions.

DISCLOSURE OF THE INVENTION

The invention firstly relates to a cosmetic method for dyeing or making up keratin fibres, in particular eyelashes and/or eyebrows and preferably eyebrows, comprising the application onto said keratin fibres of at least:
a) A cosmetic dyeing composition A comprising, in a physiologically-acceptable medium, one or more natural dyes selected from the group consisting of neoflavonoids, gallic tannins and catechetic tannins, proanthocyanidins and derivatives of same, and mixtures thereof, or preferably one or more plant extracts containing them, and advantageously an antioxidant agent,
b) A revealing cosmetic composition B comprising, in a physiologically-acceptable medium, at least one iron salt and/or aluminum salt, in particular iron gluconate or iron sulphate.

composition A being applied before or after composition B, preferably before composition B.

According to a particular and preferred embodiment, composition A also comprises an agent promoting and/or increasing the penetration of the natural dye into the keratin fibres, in particular eyelashes and/or eyebrows and preferably eyebrows, chosen from among bicyclic ethers, fatty acid esters comprising polyethoxylated C6 to C18 hydrocarbon chains, and mixtures thereof, preferably bicyclic ethers, each ring of the bicyclic molecule comprising a number n of members between 3 and 10, fatty acid esters comprising a saturated or unsaturated, linear or branched (using other C6 to C18 hydrocarbon chains) C6 to C18 hydrocarbon chain each of the hydrocarbon chains being polyethoxylated, with a degree of ethoxylation of at least 2, especially from 2 to 12, and mixtures thereof, more preferably dimethyl isosorbide, PEG-7 glyceryl cocoate, and mixture thereof.

The invention also relates to a kit or device for dyeing or making up keratin fibres, in particular eyelashes and/or eyebrows and preferably eyebrows, with several separate compartments and comprising:
   in one compartment, dyeing composition A as defined in the invention
   in another separate compartment, revealing composition B such as defined in the invention and characterized in that it does not comprise the iron and/or aluminum salt, and
   in another separate compartment, the iron and/or aluminum salt intended to be mixed extemporaneously with revealing composition B before application onto keratin fibres,
   and, advantageously, instructions for use.

According to an alternative, the kit or device for dyeing or making up keratin fibres, in particular eyelashes and/or eyebrows and preferably eyebrows, with several separate compartments comprises:
   in one compartment, dyeing composition A as defined in the invention;
   in another separate compartment, revealing composition B such as defined in the invention and characterized in that it does comprise the iron and/or aluminum salt,
   and, advantageously, instructions for use.

The kits according to the invention could also comprise, optionally, in another separate compartment, a composition C comprising an oxidant for a pretreatment of the keratin fibres before treatment with compositions A and B. Indeed, it is known that an oxidant such as hydrogen peroxide produces a slight alteration of the cuticles or scales, outer part of keratin fibres, to open them up and allow the active ingredients to penetrate better. In the context of the invention, the use of a pretreatment with an oxidant promotes better penetration of the dyeing agents.

BRIEF DESCRIPTION OF THE DRAWINGS

FIG. 1A is a microscopy image of an untreated fiber characterized by a white halo (white border).

FIG. 1B is a microscopy image of a treated keratin fiber, treated with a composition A1 comprising DMI, and characterized by a black halo.

FIG. 1C is a microscopy image of a treated keratin fiber, treated with cationic dyes without DMI.

FIG. 1D is a microscopy image of a treated keratin fiber, treated with phospholipids.

DETAILED DESCRIPTION OF THE INVENTION

The invention therefore concerns a cosmetic method for dyeing or making up keratin fibres, in particular eyelashes and/or eyebrows and, preferably, eyebrows, comprising the application onto said keratin fibres of at least:
- a) A cosmetic dyeing composition A comprising, in a physiologically-acceptable medium, one or more natural dyes selected from the group consisting of neoflavonoids, gallic tannins and catechetic tannins, proanthocyanidins and derivatives of same, and mixtures thereof, or preferably one or more plant extracts containing them, and advantageously an antioxidant agent,
- b) A revealing cosmetic composition B comprising, in a physiologically-acceptable medium, at least one iron salt and/or aluminum salt, in particular iron gluconate or iron sulphate.

composition A being applied before or after composition B, preferably before composition B.

Oxidant Pretreatment (Optional)

According to a first embodiment of the invention, compositions A and B do not contain an oxidant agent and the keratin fibres are not treated with an oxidant before or after treatment with compositions A and B.

According to another embodiment, the keratin fibres, in particular the eyelashes and/or eyebrows and preferably eyebrows, are pretreated with an oxidant before the application of said compositions A and B. As indicated above, this oxidant pretreatment opens up the scales of the keratin fibres and promotes penetration of the dyes.

The oxidant can be chosen from among the group made up of hydrogen peroxide, urea peroxide, alkali metal bromates or ferricyanides, preoxygenated salts such as, for example, persulphates, perborates, peracids and precursors thereof and alkali or alkaline earth metal percarbonates. Preferably, hydrogen peroxide is used.

In particular, a pretreatment composition C is applied onto keratin fibres, in particular eyelashes and/or eyebrows and preferably eyebrows, comprising hydrogen peroxide as an oxidant before the application of dyeing composition A and revealing composition B. The Applicant has shown that pretreatment with an oxidant makes it possible to improve the intensity and longevity of the colour.

The oxidant can be present in pretreatment composition C in a content ranging from 1% to 15% by weight, preferably from 1% to 12% by weight, relative to the total weight of the composition.

In particular, the composition comprises 1% to 12% by weight of hydrogen peroxide or, by volume, 3 volumes to 40 volumes of the total composition.

Dyeing Cosmetic Composition A

Dyeing cosmetic composition A according to the invention comprises one or more natural dyes selected from the group consisting of neoflavonoids, gallic tannins and catechetic tannins, proanthocyanidins and derivatives of same, and mixtures thereof, or, preferably, one or more plant extracts containing them. In particular, natural dye(s) suitable for the invention can be chosen from among haematoxylin, haematein, brazilein, brazilin, gallic acid, catechin, castalagin, vescalagin, procyanidins, and mixtures thereof.

Plant Extracts Comprising Polyphenols

Plant extracts usable according to the invention are plant extracts comprising at least polyphenols selected from the group consisting of neoflavonoids, gallic tannins and catechetic tannins, proanthocyanidins and derivatives of same, and mixtures thereof. These polyphenols are predominant in the composition of said plant extracts.

In particular, the plant extracts suitable for the invention are chosen from plant extracts containing at least one dye selected from the group consisting of haematoxylin, haematein, brazilein, brazilin, gallic acid, catechin, castalagin, vescalagin and procyanidins.

The following plant extracts can especially be used (genus and species):
- Logwood (*Haematoxylon campechianum*) or Mexican logwood (*Haematoxylon brasiletto*) especially containing gallic tannins (or gallotannins) and flavonoids/neoflavonoids;
- Chestnut (*Castanea sativa*) extract especially containing hydrolyzable ellagitannin tannins such as vescalagin and castalagin and gallic tannins such as gallic acid monomers and derivatives;
- Nutgall (*Rhus semialata* gall extract) or *Anogeissus* bark, in particular containing gallic acid ellagitannin and derivatives;
- tea, pine or grapevine extracts especially comprising condensed proanthocyanidin tannins and, in particular, catechin and catechetic derivatives thereof for tea and grapevine (procyanidolic oligomers OPC);
- cacao extract;
- sorghum extract especially containing anthocyanins and gallic and catechetic tannins;
- myrobalan extract (*Terminalia chebula* fruit extract) especially containing gallic acid
- hibiscus and strawberry extracts especially containing anthocyanins, and mixtures thereof.

Thus, according to a particular embodiment of the invention, dyeing composition A comprises a natural dye selected from the group consisting of haematoxylin, haematein, brazilein, brazilin, gallic acid, catechin, castalagin, vescalagin, and/or procyanidins and mixtures thereof, or a plant extract containing them, in particular a plant extract selected from the group consisting of a logwood extract, a Mexican logwood extract, a chestnut extract, a nutgall extract (*Rhus semialata* gall extract), an *Anogeissus* bark extract, a pine extract, a tea extract, a grapevine extract, a sorghum extract, a cacao extract, a myrobalan extract, a hibiscus extract, a strawberry extract and mixtures thereof, preferably a logwood extract, a Mexican logwood extract, a chestnut extract, and mixtures thereof.

According to a particular and preferred embodiment, dyeing composition A comprises at least one plant extract chosen from among a logwood extract, a chestnut extract, a Mexican logwood extract and mixtures thereof.

The extracts are obtained by extraction of various plant parts, such as, for example, the root, wood, bark or leaf.

In particular, the following will be used: a logwood wood extract, a chestnut wood or bark extract, a sorghum leaf or stem extract, a pine bark extract, a tea leaf extract, a nutgall extract, a cocoa bean extract, a Mexican logwood wood or bark extract and mixtures thereof.

According to a first embodiment, dyeing composition A comprises at least one logwood extract. In particular the logwood extract (*Haematoxylum Campechianum*) from the company SCRD is used, also known by the name Hematin NO200. It is a dark brown to burgundy powder comprising 20-40% of haematoxylin (neoflavanoid type polyphenol) by dry weight. It is a pure, non-oxidized plant dye obtained from logwood wood. The degree of oxidation originates from the natural oxidation of the haematoxylin contained in the product with no chemical oxidation.

The logwood extract is primarily made up of haematoxylin dye, glucosides and tannins, more or less condensed. The chemical structure of the two main dyes, haematoxylin and haematein, allows them to be classified in the neoflavanoid group. The range of colours that can be obtained with the logwood extract is one of the broadest of plant dyes.

According to another particular embodiment, dyeing composition A comprises at least one chestnut wood or bark extract with the INCI name Castanea sativa (chestnut) bark extract. Chestnut bark and wood especially contain eight polyphenol compounds, including ellagitannins, castalin, vescalagin, castalagin, acutissimin A, kurigalin and chestanin. In particular, a chestnut wood extract can be used obtained by aqueous extraction of the wood, filtration, concentration and drying, such as sold by the company Couleurs de Plantes.

According to another particular embodiment, dyeing composition A comprises at least one Mexican logwood extract. The Mexican logwood (*Haematoxylum Brasiletto* or *Brasiliensis*) is a small tree (2 to 12 metres) commonly present throughout Central America. Mexican logwood extract is rich in brazilin (its oxidized form is brazilein). A Mexican logwood extract sold by the company SCRD can especially be used.

Dyeing composition A can also comprise a mixture of plant extracts according to the invention, depending on the shade sought. According to a particular embodiment, dyeing composition A comprises a mixture of logwood extract and chestnut extract.

The natural dye(s) or the plant extract(s) containing them are present in dyeing composition A of the invention in a total content ranging from 0.1 to 10%, preferably 2 to 5% by weight relative to the total weight of the composition. The skilled person will adjust the total plant extract content to be used in the composition depending on the effect sought and the nature and content of the natural dye(s) of said extracts.

Antioxidant Agent (Oxidation Reducing Agent)

Dyeing composition A also advantageously comprises at least one antioxidant (also called oxidation reducing agent). This antioxidant both protects the plant extract from oxidation and acts on the keratin fibre, and in particular the eyebrow, to break disulfide bridges and thus improve the colour.

The antioxidant can especially be chosen from among sulfites, bisulfites, thiols and phosphines, preferably sulfites and bisulfites of alkali metals or alkaline-earth metals. Sodium sulfite or bisulfite can be particularly mentioned.

According to a particular and preferred embodiment, dyeing composition A comprises a sodium bisulfite (sodium metabisulfite) as antioxidant.

The antioxidant can be present in dyeing composition A in a content ranging from 0.01 to 0.5%, preferably from 0.05 to 0.1% by weight, relative to the total weight of said composition.

Agent Promoting and/or Increasing the Penetration of the Dye (Also Called Penetration Booster))

According to a particular and preferred embodiment, composition A also comprises an agent promoting and/or increasing the penetration of the natural dye into keratin fibres, in particular eyelashes and/or eyebrows and preferably eyebrows.

The Applicant has shown, as illustrated in the examples below, that the use of certain agents increasing the penetration of the natural dye into keratin fibre improves the properties of the dye or its longevity. The terms agent promoting and/or increasing penetration of the natural dye or natural dye penetration "booster" agent are used interchangeably.

This agent promoting and/or increasing penetration of the natural dye into keratin fibre, and particular the eyebrow, is different from benzylic alcohol.

This agent promoting and/or increasing penetration of the natural dye into the keratin fibre and, in particular, the eyebrow, is chosen from among bicyclic ethers, fatty acid esters comprising polyethoxylated C6 to C18 hydrocarbon chains, and mixtures thereof.

According to a particular and preferred embodiment, the agent promoting and/or increasing the penetration of the natural dye into the keratin fibre is chosen from among bicyclic ethers, each ring of the bicyclic molecule comprising a number n of members between 3 and 10, fatty acid esters comprising a saturated or unsaturated, linear or branched (using other C6 to C18 hydrocarbon chains) C6 to C18 hydrocarbon chain, each of the hydrocarbon chains being polyethoxylated, with a degree of ethoxylation of at least 2, especially from 2 to 12, and mixtures thereof.

According to a particular and preferred embodiment. the bicyclic ether is dimethyl isosorbide. According to another particular and preferred embodiment, the polyethoxylated fatty acid ester is PEG-7 glyceryl cocoate.

According to a particular embodiment, dyeing composition A comprises at least dimethyl isosorbide, such as the one sold under the names ARLASOLVE™ DMI or GRANSOLVE™ DMI by the company CRODA, Dottisol™ by the company Dottikon ES AG, NEX-DMI™ by the company Nexgen Biotechnologies, Inc; or OriStar DMI™ by the company Orient Stars LLC.

According to another particular embodiment, dyeing composition A comprises at least PEG-7 glyceryl cocoate, such as the one sold under the names CETIOL® HE by the company BASF, or Chemonic LI-7 Surfactant by the company Lubrizol Advanced Materials, Inc, or Tegosoft GC by the company Evonik Nutrition & Care GmbH or Nikkol SG-CG700 by the company Nikko Chemicals Co., Ltd or Glycerox HE by the company Croda.

Dyeing composition A can also comprise aromatic alcohols, especially chosen from among benzyl alcohol, phenyl ethanol and phenyl propanol, as preservatives. According to a particular embodiment, dyeing composition A also comprises phenoxyethanol and benzyl alcohol as preservatives.

The preservative content can range from 0.1 to 5%, in particular from 0.3 to 3% and preferably from 0.5 to 2% by weight relative to the total weight of said composition.

Nonionic Surfactant

Dyeing composition A can also advantageously comprise a nonionic surfactant, in particular an alkyl glucoside, preferably decyl glucoside.

As nonionic surfactant usable in dyeing composition A of the invention, alkylpolyglucosides can particularly be mentioned.

According to a particular embodiment, an alkyl glucoside can be used as nonionic surfactant according to the invention. These known surfactants of the state of the art can also be represented by the following general formula: $R_1O-(R_2O)_t(G)_v$ wherein:

R1 represents a linear or branched alkyl and/or alkenyl radical comprising approximately 8 to 24 carbon atoms, an alkylphenyl radical whose the linear or branched alkyl radical comprises 8 to 24 carbon atoms.

R2 is an alkylene radical comprising approximately 2 to 4 carbon atoms;

G represents a sugar unit comprising 5 to 6 carbon atoms, t designates a value ranging from 0 to 10, preferably 0 to 4, and v designates a value ranging from 1 to 15.

According to a particular embodiment, alkyl polyglucoside surfactants are compounds of the formula described above wherein R1 more particularly designates a saturated or unsaturated, linear or branched alkyl radical comprising 8 to 18 carbon atoms, t designates a value ranging from 0 to 3, and still more particularly equal to 0, G can designate glucose, fructose or galactose, preferably glucose. The degree of polymerization, i.e., the value of v in the formula above, can range from 1 to 15, preferably from 1 to 4. The mean degree of polymerization is more particularly comprised between 1 and 2. The glucoside bonds between sugar units are of the 1-6 or 1-4 type, and preferably 1-4.

Compounds corresponding to the formula above are notably represented by products sold by the company BASF under the names PLANTAREN® (600 CS/U, 1200 and 2000) or PLANTACARE® (818, 1200 and 2000) or LUTENSOL GD 70. Products sold by the SEPPIC company under the names TRITON CG110 (or ORAMIX CG 10) and TRITON CG312 (or ORAMIX® NS 10) can also be used.

According to a particular and preferred embodiment, dyeing composition A comprises a decyl glucoside such as the one sold under the name PLANTACARE 2000® UP or PLANTACARE 2000® UP/MB by the company BASF, or Triton CG-50 Surfactant by the Dow Chemical Company, or Blanova Tens APG 2000 by the company Azelis Deutschland Kosmetik GmbH or Oramix NS 10 by the company Seppic.

The nonionic surfactant content, preferably in alkyl polyglucoside and more preferably in decyl glucoside in dyeing composition A according to the invention will range from 0.5 to 10% by weight, preferably from 3% to 5% by weight, relative to the total weight of composition A.

Polymeric Gelling Agent

According to one particular embodiment, dyeing composition A will also comprise a polymeric gelling agent, preferably an acrylic polymeric gelling agent. The presence of this polymeric gelling agent makes it possible to structure the composition by improving its viscosity.

According to a particular embodiment, it is a "hydrophilic polymeric gelling agent", able to gel the aqueous phase of the compositions according to the invention.

The gelling agent can be water soluble or water dispersible.

The polymeric gelling agent according to the invention is preferably a synthetic polymeric gelling agent, in other words, it is not naturally existing or derived from a polymer of natural origin (e.g., polysaccharides, celluloses, etc.).

The synthetic polymeric gelling agent considered according to the invention can be particulate or not; in particular, it is present in the form of particles, preferably spherical.

Preferably, the polymeric gelling agent according to the invention is an acrylic polymer gelling agent chosen from among modified or unmodified carboxyvinyl polymers. These carboxyvinyl polymers can be copolymers resulting from polymerization of at least one monomer (a) chosen from among α,β-ethylenically unsaturated carboxylic acids or esters thereof, with at least one ethylenically unsaturated monomer (b) comprising a hydrophobic group. "Copolymers" means both copolymers obtained from two types of monomers and those obtained from more than two types of monomers such as terpolymers obtained from three types of monomers.

Their chemical structure more particularly comprises at least one hydrophilic unit and at least one hydrophobic unit. Hydrophobic group or unit means a radical with a saturated or unsaturated, linear or branched hydrocarbon chain, comprising at least 8 carbon atoms, preferably 10 to 30 carbon atoms, in particular 12 to 30 atoms and more preferentially 18 to 30 carbon atoms.

These polymeric gelling agents are, for example, acrylic and methacrylic acid polymers or copolymers such as acrylic acid/ethyl acrylate copolymers and carboxyvinyl polymers. Examples of such polymers or copolymers are, especially, "carbomers" (CTFA) sold under the name Carbopol® by the company GOODRICH or by the company LUBRIZOL. Polyglycerylmethacrylate sold by the company UNITED GUARDIAN under the name Lubrajel or polyglyceryl acrylate sold under the name Hispagel by the company HISPANO CHIMICA or finally the polyacrylamide/C13-C14 Isoparaffin/Laureth-7 mixture sold by the company SEPPIC under the name Sepigel can also be mentioned.

According to a particular embodiment, dyeing composition A comprises a polyacrylic acid homopolymer with the INCI name Carbomer.

The polymeric gelling agent content in dyeing composition A of the invention will range from 0.1 to 5% by weight, preferably from 1% to 2% by weight, with regard to the total weight of the composition.

Additional Coloring Materials

Dyeing composition A of the invention may also advantageously comprise at least one additional coloring material chosen from among pigments, dyes and mixtures thereof.

The use of these additional pigments and/or dyes especially makes it possible to obtain more colour shades.

The coloring material(s) may be chosen from water-soluble or non-water soluble, fat-soluble or non-fat-soluble, organic or inorganic coloring materials, materials with optical effects and mixtures thereof. Within the meaning of the present invention, coloring materials means a compound that can produce a coloured optical effect when it is formulated in sufficient quantity in an appropriate cosmetic medium.

According to a particular embodiment, the coloring material(s) are notably chosen from mineral and/or organic pigments, composite pigments (based on mineral and/or organic materials), dyes, and mixtures thereof.

Pigments should be understood to mean coloured inorganic (mineral) or organic particles insoluble in the organic liquid phase. Mineral pigments include, for example, black, yellow, red and brown iron oxides; manganese violet; ultramarine blue; chromium oxide; hydrated chromium oxide and Prussian blue.

Organic pigments include, for example D & C Red 19; D & C Red 9; D & C Red 22; D & C Red 21; D & C Red 28; D & C Yellow 6; D & C Orange 4; D & C Orange 5; D & C Red 27; D & C Red 13; D & C Red 7; D & C Red 6; D & C Yellow 5; D & C Red 36; D & C Red 33; D & C Orange 10; D & C Yellow 6; D & C Red 30; D &C Red 3; D &C Blue 1; carbon black and cochineal carmine lacquers.

Water soluble dyes include Yellow 5, Yellow 6, Blue 1, Green 5, Green 3, Green 6, Orange 4, Red 4, Red 21, Red 22, Red 27, Red 28, Red 33, Red 40 and cochineal carmine (CI 15850, CI 75470).

According to a particular embodiment, dyeing composition A comprises at least one coloring material chosen from among direct dyes, preferably cationic direct dyes.

These direct dyes are chosen, for example, from among aromatic and/or nonaromatic dyes commonly used such as neutral, acidic or cationic nitrobenzene direct dyes, neutral, acidic or cationic azo direct dyes, quinone direct dyes and in particular neutral, acidic or cationic anthraquinone dyes, azine direct dyes, triarylmethanes, indoamines, methines, styryls, porphyrins, metalloporphyrins, phthalocyanines, methine cyanines, and fluorescent dyes.

According to a particular and preferred embodiment, dyeing composition A will comprise one or more cationic direct dyes. The cationic direct dyes with the following INCI name can especially be mentioned: BASIC RED 76, BASIC YELLOW 57, HC BLUE NO. 15, and mixtures thereof.

The additional coloring material content, especially in direct dyes, in particular cationic direct dyes, in dyeing composition A according to the invention will generally range from 0.005 to 5% by weight, preferably from 0.005% to 0.5% by weight, with regard to the total weight of the composition.

Revealing Cosmetic Composition B

Colour revealing composition B comprises at least one iron salt and/or at least one aluminum salt. Iron salts in particular make it possible to obtain the dark shades sought, ranging from brown to black. These salts allow metal complexation onto the keratin fibre, in particular the eyebrow.

Iron and/or Aluminum Salts

According to the invention, "iron salts and/or aluminum salts" means oxides of these metals and the salts themselves, especially derived from the action of an acid on a metal. Preferably, the salts are not oxidized. Salts can include halides such as chlorides, fluorides and iodides; sulphates, phosphates; nitrates; perchlorates and carboxylic acid salts and polymer complexes that can support said salts, as well as mixtures thereof. Carboxylic acid salts usable in the invention also include hydroxylated carboxylic acid salts such as gluconate.

Iron or aluminum salts according to the invention can include sulphates, gluconates, chlorides, lactates, acetates, glycinates, aspartates and citrates.

As aluminum salts, one or more alums can be used, i.e., one or more mixed aluminum sulphates and monovalent cation, especially chosen from among aluminum and potassium sulphate (potassium alum), aluminum and sodium sulphate (sodium alum) and aluminum and ammonium sulphate (ammonium alum).

Preferably, iron gluconate, potassium, sodium or ammonium alums and mixtures of these salts will be used.

According to a particular and preferred embodiment, revealing composition B comprises at least one iron gluconate. The iron gluconate sold by the company Givaudan-Lavirotte under the name GIVOBIO Fe 601 or Gluconal FE of the company Glucona America, Inc. can especially be mentioned.

The iron and/or aluminum salt(s) used in revealing composition B advantageously represent from 0.1% to 10%, preferably 3% to 5% by weight of the total weight of the composition.

The iron salt and/or aluminum salt, preferably iron gluconate or iron sulphate, more preferably still iron gluconate, can be integrated into revealing composition B, but preferably it is added extemporaneously to revealing composition B before it is applied onto keratin fibres, in particular eyelashes and/or eyebrows and preferably eyebrows.

Film-Forming Polymer

According to a particular embodiment, revealing composition B comprises at least one film-forming polymer.

This film-forming polymer makes it possible to improve the longevity of the dyeing or making up of keratin fibres, in particular eyelashes and/or eyebrows and, preferably, eyebrows.

This film-forming polymer can especially be chosen from among the cationic, anionic, amphoteric or nonionic polymers conventionally used in the hair care field, or among the film-forming polymers used in the mascara field.

According to a particular embodiment, the film-forming polymer is chosen from among acrylic copolymers.

In particular, an aqueous dispersion of the C1-C6 nonionic film-forming polymer alkyl (meth)acrylate can be mentioned, and especially the polymer essentially consisting of one or more C1-C6 alkyl (meth)acrylates. These polymers can be chosen from among C1-C4 alkyl (meth)acrylate polymers and, in particular, C1-C4 alkyl acrylate and C1-C4 alkyl methacrylate copolymers and mixtures thereof. C1-C4 alkyl (meth)acrylates include methyl methacrylate, ethyl methacrylate, propyl methacrylate and butyl methacrylate. Preferably, an ethyl acrylate and methyl methacrylate copolymer can be used, such as the one sold under the name "DAITOSOL 5000 AD" by the company DAITO KASEY KOGYO.

Other examples of polymers usable according to the invention include:

ACRYLATES/ETHYLHEXYL ACRYLATE copolymer sold under the name Daitosol 5000 SJT® by the company Daito Kasei, SODIUM STYRENE/ACRYLATES COPOLYMER sold under the name Daitosol 5000 STY® by the company Daito Kasei, ACRYLATES/ETHYLHEXYL ACRYLATE COPOLYMER sold under the name Daitosol 4000 SJT by the company Daito Kasei, ACRYLATES copolymer sold under the name Daitosol 5000 AD® by the company Daito Kasei.

The film-forming polymer advantageously used in revealing composition B can be present in a content ranging from 1% to 10%, preferably from 1% to 5% by weight (of the dry polymer extract) of the total weight of the composition.

Formulations

The various compositions of the invention described above can be found independently of one another in various formulations, such as a powder, a lotion, a foam, a cream, an emulsion, a gel or any other appropriate form to dye keratin fibres, in particular eyebrows.

They will preferably be applied onto keratin fibres, in particular eyelashes and/or eyebrows, and preferably eyebrows, using a pencil or a brush.

The compositions used in the method according to the invention comprise an appropriate medium for dyeing or making up keratin fibres, which can contain water or a mixture of water and one or more organic solvents.

Preferably, compositions A and B used in the method according to the invention each comprise water or a mixture of water and one or more organic solvents.

$C_1$-$C_4$ mono-alcohols can be mentioned as organic solvent, such as ethanol and isopropanol; polyols and polyol ethers such as 2-butoxyethanol, propylene glycol, propylene glycol monomethyl ether, diethylene glycol monoethyl ether and monomethyl ether, hexylene glycol, as well as aromatic alcohols such as benzyl alcohol or phenoxyethanol. The organic solvents are generally present in the compositions of the invention in a content ranging from 0.1 to 5%, preferably from 1% to 2% by weight relative to the total weight of the composition.

The compositions of the invention can also include various additives such as antioxidants, sequestrants, fragrances, pH adjusters (also called acidifiers or alkalinizers), dispersants, conditioning agents and mixtures thereof.

pH Adjustment (for Compositions A and/or B)

Dyeing composition A and/or revealing composition B advantageously comprise a pH adjuster.

Preferably, the pH of said compositions will range from 6 to 8.5, preferably 7 to 8.

According to a particular embodiment, the pH of the composition ranges from 7 to 7.5.

The pH of the compositions used in the method according to the invention can thus be adjusted to the desired value using the acidifiers or alkalinizers commonly used in cosmetics or even using conventional buffer systems. Acidifiers for the compositions used in the invention include, for example, citric acid. One advantageous variant is to add an alkalizer to the composition(s) for the method according to the invention, containing (bi)carbonate(s). More particularly, this alkaline agent is chosen from among ammonia, alkaline carbonates or bicarbonates such as alkaline sodium or potassium carbonates or bicarbonates, alkanolamines such as mono-, di- and triethanolamines as well as derivatives thereof, sodium or potassium hydroxides, and mixtures thereof. The skilled person will choose to adjust the pH suited to the area of application of the eyebrow (eye area).

According to a particular and preferred embodiment of the invention, the composition(s) of the invention comprise alkaline bicarbonates, in particular sodium bicarbonate.

Particular Formulation in the Form of Aqueous Gels

According to a particular embodiment of the invention, dyeing composition A and revealing composition B are in the form of gels, preferably in the form of aqueous gels.

These aqueous gels are characterized by an aqueous phase generally comprising water and water-soluble organic solvents such as described previously, and one or more gelling agents, preferably acrylic polymeric gelling agents.

The presence of these polymeric gelling agents makes it possible to structure compositions A and B by improving their viscosity. Preferably, the viscosity of compositions A and B will range from 2000 cps to 10,000 cps, preferably from 4000 cps to 7000 cps, measured with a RheolabQC rotational rheometer.

According to a particular embodiment, dyeing composition A also comprises a polymeric gelling agent, such as described previously. Preferably, the polymeric gelling agent used according to the invention is not a natural polymeric gelling agent (e.g., polysaccharides, celluloses, etc.).

Preferably, the polymeric gelling agent used according to the invention is an acrylic polymeric gelling agent. These polymeric gelling agents are, for example, acrylic and methacrylic acid polymers or copolymers such as acrylic acid/ethyl acrylate copolymers and carboxyvinyl polymers. Examples of such polymers or copolymers are, especially, "carbomers" (CTFA) sold under the name Carbopol® by the company GOODRICH or by the company LUBRIZOL. Polyglycerylmethacrylate sold by the company UNITED GUARDIAN under the name Lubrajel or polyglyceryl acrylate sold under the name Hispagel by the company HISPANO CHIMICA or finally the polyacrylamide/C13-C14 Isoparaffin/Laureth-7 mixture sold by the company SEPPIC under the name Sepigel can also be mentioned.

According to a particular embodiment, dyeing composition A comprises a polyacrylic acid homopolymer with the INCI name Carbomer.

The polymeric gelling agent content in dyeing composition A of the invention will generally range from 0.1 to 3% by weight, preferably from 1% to 2% by weight, with regard to the total weight of the composition.

According to a particular and preferred embodiment, revealing composition B comprises a hydrophilic polymeric gelling agent chosen from among associative polymers.

This polymeric gelling agent in revealing composition B in the form of a gel makes it possible to improve the stability of the composition, in particular on contact with iron gluconate, which is likely to impact the stability and/or structure of said composition.

According to a particular and preferred embodiment, revealing composition B in the form of aqueous gel comprises at least one associative polymer.

According to the present invention, "associative polymer" means any amphiphilic polymer comprising in its structure at least one fatty chain and at least one hydrophilic portion. The associative polymers conforming to the present invention can be anionic, cationic, nonionic or amphoteric. Preferably, it will be an anionic associative polymer.

Anionic associative polymers include those comprising at least one hydrophilic unit, and at least one allyl ether unit with a fatty chain, more particularly among those whose hydrophilic unit is made up of an ethylenically-unsaturated anionic monomer, more particularly by a vinyl carboxylic acid and most particularly by an acrylic acid, a methacrylic acid, or mixtures thereof, and whose allyl ether unit with a fatty chain corresponds to the monomer of formula (I) below:

$$CH_2=C(R')CH_2OB_nR \qquad (I)$$

wherein R' designates H or $CH_3$, B designates the ethyleneoxy radical, n is zero or designates a whole number from 1 to 100, R designates a hydrocarbon radical chosen from among alkyl, arylalkyl, aryl, alkylaryl and cycloalkyl radicals, comprising 8 to 30 carbon atoms, preferably 10 to 24, and more particularly still 12 to 18 carbon atoms.

Associative anionic polymers, can also include maleic anhydride/$C_{30}$-$C_{38}$ α-olefin/alkyl maleate terpolymers such as the maleic anhydride/$C_{30}$-$C_{38}$ α-olefin/isopropyl maleate copolymer product sold under the name PERFORMA V 1608 by the company NEWPHASE TECHNOLOGIES.

Anionic associative polymers include, according to a preferred embodiment, copolymers comprising among their monomers an α,β-monoethylenically unsaturated carboxylic acid and an α,β-monoethylenically unsaturated carboxylic acid ester and an oxyalkylenated fatty alcohol. Preferentially, these compounds also comprise as monomer an α,β-monoethylenically unsaturated carboxylic acid ester and a C1-C4 alcohol.

Examples of this type of compound can include ACULYN 22® sold by the company ROHM and HAAS, which is an methacrylic acid/ethyl acrylate/oxyalkylenated stearyl methacrylate terpolymer (comprising 20 OE units) or ACULYN 28 (methacrylic acid/ethyl acrylate/behenyl oxyethylene methacrylate terpolymer (25 OE).

Anionic associative polymers can also include anionic polymers comprising at least one hydrophilic unit of the unsaturated olefinic carboxylic acid type, and at least one hydrophobic unit exclusively of the unsaturated (C10-C30) carboxylic acid alkyl ester type.

Anionic associative polymers can also include anionic terpolymers.

The anionic terpolymer can be a linear or branched and/or crosslinked terpolymer, at least one monomer (1) bearing an acid function in the free, partially or totally salified form, with a nonionic monomer (2) chosen from N,N-dimethylacrylamide and 2-hydroxyethyl acrylate and at least one polyoxyethylenated alkyl acrylate monomer (3) of the following formula (II):

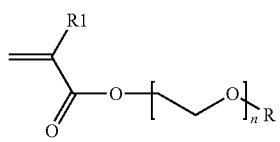
(II)

wherein R1 is a hydrogen atom, R is a linear or branched $C_2$-$C_8$ alkyl radical and n is a number ranging from 1 to 10.

"Branched polymer" means a nonlinear polymer that has hanging chains so that, when this polymer is dissolved in water, a high state of entanglement is obtained, leading to very high viscosities at low speed gradient.

"Cross-linked polymer" means a nonlinear polymer in the state of a three-dimensional network insoluble in water, but that swells with water and therefore results in a chemical gel.

The monomer (1) acid function is especially the sulfonic acid or phosphonic acid function, said functions being in the free, partially or totally salified form.

Monomer (1) can be chosen from among styrenesulfonic acid, ethylsulfonic acid or 2-methyl-2[(1-oxo-2-propenyl)amino] 1-propanesulfonic acid (also called acryloyldimethyltaurate) in free, partially or totally salified form. It is present in the anionic terpolymer preferably in molar proportions comprised between 5% and 95% molar and more particularly between 10% and 90% molar. Monomer (1) will more particularly be 2-methyl-2-[(1-oxo-2-propenyl)amino] 1-propanesulfonic acid in free, partially or totally salified form.

The acid function in the partially or totally salified form will preferably be an alkali metal salt such as a sodium or potassium salt, an ammonium salt, an aminoalcohol salt such as a monoethanolamine salt or even an amino acid salt such as a lysine salt.

Monomer (2) is preferably present in the anionic terpolymer in molar proportions comprised between 4.9% and 90% molar and more particular between 9.5% and 85% molar and still more particularly between 19.5% and 75% molar.

In formula (II), examples of a linear $C_8$-$C_{16}$ alkyl radical include octyl, decyl, undecyl, tridecyl, tetradecyl, pentadecyl and hexadecyl.

In formula (II), examples of a branched $C_8$-$C_{16}$ alkyl radical, include 2-ethylhexyl, 2-propylheptyl, 2-butyloctyl, 2-pentylnonyl, 2-hexyldecyl, 4-methylpentyl, 5-methylhexyl, 6-methylheptyl, 15-methylpentadecyl, 16-methylheptadecyl and 2-hexyloctyl.

According to a particular form of the invention, in formula (I), R designates a C12-C16 alkyl radical.

According to a particular form of the invention, in formula (I), n varies from 3 to 5.

Tetra-ethoxylated lauryl acrylate can particularly be used as a monomer of formula (II).

Monomer (3) of formula (II) is preferably present in the anionic terpolymer in molar proportions comprised between 0.1% and 10% molar and more particularly between 0.5% and 5% molar.

According to a particular embodiment of the invention, the anionic terpolymer is crosslinked and/or branched by a diethylene or polyethylene compound in the proportion, expressed relative to the total quantity of monomers used, of 0.005% to 1% molar and preferably 0.01% to 0.5% molar and more particularly 0.01% to 0.25% molar.

The crosslinking agent and/or branching agent is preferably chosen from among ethylene glycol dimethacrylate, diallyloxoacetic acid or one of its salts, such as sodium diallyloxyacetate, tetraallyloxyethane, ethylene glycol diacrylate, diallyl urea, triallyl amine, trimethylolpropane triacrylate, methylenebis(acrylamide) or mixtures thereof.

The anionic terpolymer can contain additives such as complexing agents, transfer agents, or chain-limiting agents.

In revealer composition B of the invention, an anionic terpolymer of 2-methyl-2-[(1-oxo-2-propenyl)amino] 1-propanesulfonic acid, partially or totally salified in the form of ammonium salt, N,N-dimethylacrylamide and tetraethoxylated lauryl acrylate crosslinked with trimethylol propanetriacrylate can be used, with INCI name Polyacrylate Crosspolymer-6 such as the product sold under the brand name SEPIMAX ZEN® by the company SEPPIC.

The hydrophilic gelling agent, in particular the anionic associative polymer present in revealing composition B, will be present in a content ranging from 0.1% to 5% by weight, preferably from 1% to 3% by weight, relative to the total weight of the composition.

Implementation of the Dyeing or Making Up Method

Compositions A and B can be applied onto keratin fibres, in particular eyelashes and/or eyebrows, preferably eyebrows, separately and, in particular, sequentially, regardless of their order of application (application of composition A then composition B or application of composition B then composition A). According to a particular and preferred embodiment, dyeing composition A is applied before revealing composition B.

The keratin fibres, preferably eyebrows, may or may not be previously moistened. Preferably, dyeing composition A is applied onto keratin fibres that have not been previously moistened.

The keratin fibres, preferably eyebrows, may or may not be previously treated with an oxidant. According to a first embodiment, dyeing composition A will be applied onto keratin fibres that have not been previously treated with an oxidant. According to another embodiment, dyeing composition A will be applied onto keratin fibres previously treated with an oxidant, in particular hydrogen peroxide.

The application of compositions A and B can be preceded or followed by a step of rinsing and/or drying the keratin fibres. According to a particular embodiment, the method does not comprise a rinsing and/or drying step before application of compositions A and B. According to a preferred embodiment, the method nevertheless comprises a final rinsing step after application of composition B.

The exposure time after application of dyeing composition A generally varies from 30 seconds to 30 minutes, preferentially from 45 seconds to 10 minutes, and more preferentially from 1 minute to 6 minutes.

The exposure time after application of revealing composition B generally varies from 30 seconds to 10 minutes, preferentially from 45 seconds to 5 minutes.

Compositions A and B are generally applied at ambient temperature.

Thus, the invention also relates to a cosmetic method for dyeing or making up keratin fibres, in particular eyelashes and/or eyebrows and preferably eyebrows, in which:

dyeing composition A is applied onto keratin fibres, in particular eyelashes and/or eyebrows and preferably eyebrows, with an exposure time ranging from 30 seconds to 30 minutes, preferentially from 45 seconds to 10 minutes, preferentially from 1 minute to 6 minutes, revealing composition B is applied onto keratin fibres, in particular eyelashes and/or eyebrows and preferably eyebrows, with an exposure time ranging from 30 seconds to 10 minutes, preferentially from 45 seconds to 5 minutes, composition A being applied before or after composition B, preferably before composition B, said keratin fibres, in particular the eyelashes and/or eyebrows and preferably eyebrows, then being optionally rinsed in a final step.

According to a particular and preferred embodiment, dyeing composition A is applied before revealing composition B. According to a first embodiment, dyeing composition A is applied onto keratin fibres that have not been previously treated with an oxidant.

According to another embodiment, dyeing composition A is applied onto keratin fibres previously treated with an oxidant, preferably hydrogen peroxide. The pretreatment time with the oxidant will generally range from 30 seconds to 10 minutes, preferentially from 30 seconds to 5 minutes. And according to a particular embodiment, an intermediate rinsing step and optional drying is performed between the pretreatment step with the oxidant and the treatment step with the dyeing composition.

Kit or Device

The invention also relates to a kit or device for dyeing or making up keratin fibres, in particular eyelashes and/or eyebrows and preferably eyebrows, with several separate compartments and comprising:

in one compartment, dyeing composition A as defined in the invention;

in another separate compartment revealing composition B such as defined in the invention and characterized in that it does not comprise the iron and/or aluminum salt, and in another separate compartment, the iron and/or aluminum salt intended to be mixed extemporaneously with revealing composition B before application onto keratin fibres, optionally, in another separate compartment, a composition C comprising an oxidant for pretreatment of keratin fibres before treatment with compositions A and B, and, advantageously, instructions for use.

According to an alternative embodiment, the kit or device according to the invention comprises:

in one compartment, dyeing composition A as defined in the invention;

in another separate compartment, revealing composition B such as defined in the invention and characterized in that it does comprise the iron and/or aluminum salt, optionally, in another separate compartment, a composition C comprising an oxidant for pretreatment of keratin fibres before treatment with compositions A and B, and, advantageously, instructions for use.

According to a preferred embodiment, the kit or device according to the invention comprises:

dyeing composition A comprising i. a natural dye selected from the group consisting of a logwood extract, a chestnut extract, a sorghum extract, a pine extract, a tea extract, a nutgall extract, a cacao extract, a Mexican logwood extract, and mixtures thereof;

ii. a decyl glucoside as a nonionic surfactant;

iii. a sodium metabisulfite as an antioxidant;

iv. an acrylic polymer as a gelling agent, v. a pH adjuster, and vi. optionally, black pigments and/or cationic direct dyes;

revealing composition B comprising vii. an acrylic polymer as a gelling agent, viii. a pH adjuster, and ix. optionally, a film-forming polymer, a separate composition comprising iron gluconate as iron salt, and optionally, a separate composition comprising hydrogen peroxide as optional oxidant.

Compositions A and B are as described previously.

According to a particular embodiment, compositions A and B are in the form of an aqueous gel, composition A comprising an aqueous phase gelled by a carboxyvinyl polymer and composition B comprising an aqueous phase gelled by an associative polymer, in particular an anionic associative polymer.

The compositions of the kit are packaged in separate compartments, optionally accompanied by appropriate application means, identical or different, such as pencils, brushes or sponges.

According to a particular and preferred embodiment, the kit comprises a pencil or a brush for application of the compositions of the invention.

The present invention now will be illustrated by the following nonlimiting examples. Unless otherwise indicated, the percentages are expressed as percentage by weight relative to the total weight of the composition.

EXAMPLES

Example 1: Eyebrow Dye Formulations

First Composition Comprising Logwood Extract

| Logwood extract* | 5% |
|---|---|
| Glycerol | 5% |
| Dimethyl isosorbide (DMI) | 1% |
| Carbomer (Carbopol Ultrez 30) | 1.2% |
| Alkyl glucoside | 4% |
| Sodium hydroxide (10% solution) | 7% |
| Benzylic alcohol | 0.8% |
| Sodium metabisulfite | 0.05% |
| Preservatives | qs |
| Demineralized water qs | 100% |

*Logwood extract from the company SCRD

Dyeing composition A is prepared according to the following operating procedure:

dimethyl isosorbide, glycerol, sodium metabisulfite and preservatives are mixed with water with stirring;

carbomer (gelling agent) is then added to the preceding phase and mixed until complete dissolution;

then 10% sodium hydroxide is added to the solution; the formula thickens immediately;

then the logwood wood extract is added and mixed until complete dissolution;

finally, the alkyl glycoside surfactant and water are added and the gel obtained is homogenized;
the pH is verified to be between 7 and 7.5.

Revealing Composition B Comprising Iron Gluconate

| | |
|---|---|
| Thickening polyacrylate polymer (Polyacrylate Crosspolymer-6, SEPIMAX ZEN ® from SEPPIC) | 0.5% |
| Sodium carbonate | 0.5% |
| Benzylic alcohol | 0.8% |
| Preservatives | qs |
| Demineralized water | qs 100% |
| Iron gluconate | 3.6% |

Revealing composition B is prepared according to the following operating procedure:
the ingredients, except for the gelling agent and iron gluconate are mixed with stirring until complete dissolution;
then the gelling agent is added until complete dissolution and formation of the gel;
iron gluconate is added extemporaneously to composition B, before applying the product onto the eyelashes Application onto the eyelashes is done according to the following operating procedure:
dyeing composition A is applied onto the eyelashes using a pencil or brush, with an exposure time of 4 to 6 minutes;
then revealing composition B is applied onto the eyelashes using a pencil or brush, with an exposure time of 2 minutes;
then the eyelashes are rinsed.

A brown colour is obtained on the eyelashes with good longevity.

Example 2: Selection of Penetration Booster Agents, Alone or in Combination, on the Longevity of the Colour on the Eyelash The applicant has shown that the use of one or more penetration booster agents made it possible to improve the colour result on the eyebrows and its longevity. They tested different agents including phospholipids, ceramides, saponins and fatty acids then selected among the best performing agents especially dimethyl isosorbide (Arlasolve DMI from Univar) and PEG-7 Glyceryl Cocoate (Cetiol® HE from BASF).

The results presented below respectively illustrate the effect of phospholipids and dimethyl isosorbide.

2.1 Effect of Dimethyl Isosorbide Compared to Phospholipids

Different compositions are tested on a panel of 10 individuals.
Composition A1: logwood extract and +2% DMI
Composition A2: logwood extract+cationic dyes (small quantity) with no DMI
Composition A3: logwood extract+lecithin (phospholipid) 1%
Composition B: comprising iron gluconate
Compositions A1 to A3 are prepared according to Example 1 and composition B corresponds to the example described in Example 1.
Compositions A1 to A4 are applied for 4 minutes.
Composition B is applied for 2 minutes.
The effect of the presence or absence of the colour penetration booster agent in dyeing composition A is evaluated by microscopic observation on sections of keratin fibres treated or untreated by said compositions (FIG. 1). An untreated fibre is characterized by a white halo (white border), while a treated fibre (dyed) is characterized by a black halo. The thicker this halo, the deeper the diffusion of the colour into the keratin fibre.

The results are shown in FIG. 1: FIG. 1a corresponds to the untreated condition; a thicker coloured halo is observed in FIG. 1b (treated with a composition A1 comprising DMI), compared to treatments with cationic dyes without DMI (FIG. 1c) or phospholipids (FIG. 1d).

These results show that dimethyl isosorbide promotes and/or increases the penetration of the natural dye (logwood) into the keratin fibres in an improved manner compared to phospholipids.

2.2 Effect of Dimethyl Isosorbide (DMI)

Compositions similar to those described in Example 1 are reproduced; two natural dyes are used at a total content of 5%, i.e. a logwood extract (SCRD) and a chestnut extract (for example the one from the company Couleurs de plantes) in a 60/40 proportion (60% logwood extract and 40% chestnut extract).

In the comparative composition (no DMI), DMI is replaced by water.

The two compositions are evaluated at T0, T3, T7, T9 and T21 (expressed in days) according to the colour parameters L (intensity) and delta E1 (longevity) using the image capture device Visia and the image analysis software Visilog.

Values are obtained for the colorimetric parameters:
"L*" which is the luminosity of the eyebrow colour
"a*" (green/red component) and "b*" (blue/yellow component) which corresponds to the eyebrow colour The following are measured, respectively:
the difference of the perception of the colour relative to time "0" (=time before application): Delta E0 $(\Delta E0) = \sqrt{((L0-Li)^2 + (a0-ai)^2 + (b0-bi)^2)}$ and
the difference of the perception of the colour relative to time "1" (=time immediately after application): Delta E1 $(\Delta E1) = \sqrt{((L1-Li)^2 + (a1-ai)^2 + (b1-bi)^2)}$ Then the statistical analysis of these parameters (L*, Delta E0 and Delta E1) is performed.

The product longevity is validated when there is a difference between the time before application and the other measurement times for the L* and Delta E1 parameters.

The percentage of luminosity loss L* relative to the time immediately after application is calculated: %=(After-Before)/Before*100

The following results are obtained:
Assessment of colour intensity (parameter L): After application, there is no difference in terms of intensity between the two compositions. At T3, T7 and T9 days, the composition according to the invention with DMI is more intense compared to the composition without DMI. At T21, this difference is still measurable.
Assessment of colour longevity (parameter delta E1): After application, there is no difference in terms of colour intensity between the two compositions. At T3, T7, T9 and T21 days, the comparative composition without DMI has a greater colour change (delta E1) than the composition with DMI, which provides better colour longevity.

2.3 Effect of PEG-7 Glyceryl Cocoate

Example 2.1 is repeated by replacing DMI with 1% PEG-7 Glyceryl Cocoate (Cetiol HE).

Dyeing composition A is applied with an exposure time of 6 minutes. According to an alternative, it is applied with an exposure time of 3 minutes.

Similar changes are observed (parameters L and delta E1) to those observed with DMI, with improved results with an exposure time of 6 minutes: the colour intensity and longevity result lasts 21 days with an exposure time of 6 minutes, versus 9 days with an exposure time of 3 minutes.

Example 3: Effect of an Oxidant Pretreatment on the Dyeing or Making Up Result

Different compositions are tested, according to the model described in Example 1:
Composition A1: logwood extract and +1% DMI
Composition A2: logwood extract+1% Cetiol HE
Composition A3: logwood extract alone
Composition A4: logwood extract+1% DMA+1% Cetiol HE
Composition B: comprising iron gluconate Compositions A1 to A4 are prepared according to Example 1 and composition B corresponds to the example described in Example 1.

Compositions A1 to A4 are applied for 4 or 6 minutes.
Composition B is applied for 2 minutes.

These different compositions are tested with or without pretreating the keratin fibres (hair and eyebrows) with an oxidant, in particular 12% hydrogen peroxide. Pretreatment with the oxidant is performed for 2 minutes or 10 minutes. This oxidant pretreatment will open the cuticles or scales of the keratin fibres to promote better penetration of the dyes.

The effect of the oxidant pretreatment and presence of the colour penetration booster agent in dyeing composition A is evaluated by microscopic observation on treated/untreated sections of keratin fibres. A fibre untreated by the oxidant is characterized by a white halo (white border), while a treated fibre (dyed) is characterized by a black halo. The thicker this halo, the deeper the diffusion of the colour into the keratin fibre. Thus the percentage of dyed eyebrows is measured (by counting the coloured eyebrows) for each condition tested and the diffusion of the colour (thickness of the halo) is measured by using MatLab software, for eyebrows pretreated with the oxidant (eyebrows not pretreated with the oxidant do not permit such an assessment, their natural dark colour—due to the presence of melanin—does not permit documenting a colour difference).

The results (% of dyed eyebrows) are presented in Table 1 below:

TABLE 1

|  | Without oxidant pretreatment | | With oxidant pretreatment | |
| --- | --- | --- | --- | --- |
| Exposure time for compositions A and B | 4 min A then 2 min B | 6 min A then 2 min B | 4 min A then 2 min B | 6 min A then 2 min B |
| Composition A3 (without penetration booster) | 27% | 58% | 100% | 80% |
| Composition A1 (DMI 1%) | 50% | 53% | 100% | 86% |
| Composition A2 (CETIOL HE 1%) | 50% | nd | 100% | 100% |
| Composition A4 (DMI 1% + CETIOL HE 1%) | 40% | 74% | 100% | 100% | nd = not determined (not measured)

These results show that the pretreatment of eyebrows with an oxidant before application of compositions A and B increases the efficacy of dyeing: the number of eyebrows dyed after this pretreatment with oxidant is 100% for almost all the conditions, while without the oxidant pretreatment, a proportion of eyebrows are not dyed (black aureola not detectable with the microscope).

The use of the combination of DMI and Cetiol HE with an exposure time of 6 minutes for composition A and 2 minutes for composition B gives the best results, whether or not the keratin fibre was treated beforehand with an oxidant.

A microscope assessment of the thickness of dyed halos (in μm), representative of the diffusion of the colour into the fibre is done on eyebrows pretreated with the oxidant. As indicated above, eyebrows not pretreated with the oxidant do not permit such an assessment since their natural dark colour—due to the presence of melanin—does not make it possible to document a colour difference. The following results are obtained and shown in Table 2.

TABLE 2

|  | Oxidant pretreatment | |
| --- | --- | --- |
| Exposure time for compositions A and B | 4 min A then 2 min B | 6 min A then 2 min B |
| Composition A3 (without penetration booster) | 4.77 μm +/− 1.86 | 2.74 μm +/− 0.75 |
| Composition A1 (DMI 1%) | 3.68 μm +/− 0.72 | 3.66 μm +/− 0.77 |
| Composition A2 (CETIOL HE 1%) | 3.99 μm +/− 1.31 | 5.52 μm +/− 1.16 |
| Composition A4 (DMI 1% + CETIOL HE 1%) | 3.76 μm +/− 0.30 | 6.2 μm +/− 1.87 |

These results confirm that the best condition for optimal dyeing of the eyebrows is the condition 1% DMI+1% CETIOL HE with an exposure time for dyeing composition A of 6 minutes and an exposure time for revealing composition B of 2 minutes.

Example 4: Formulations and Implementation of the Method 4.1 Composition A (Dye) with a Logwood Extract

| Logwood extract* | 5% |
| --- | --- |
| Glycerol | 5% |
| Dimethyl isosorbide (DMI) | 1% |
| Carbomer (Carbopol Ultrez 30) | 1.2% |
| Alkyl glucoside | 4% |
| Sodium hydroxide (10% solution) | 7% |
| Benzylic alcohol | 0.8% |
| Sodium metabisulfite | 0.05% |
| Preservatives | qs |
| Demineralized water qs | 100% |

*Logwood extract from the company SCRD

Dyeing composition A is prepared according to the following operating procedure:

dimethyl isosorbide, glycerol, sodium metabisulfite and preservatives are mixed with water with stirring;

carbomer (gelling agent) is then added to the preceding phase and mixed until complete dissolution;

then 10% sodium hydroxide is added to the solution; the formula thickens immediately;

then the logwood wood extract is added and mixed until complete dissolution;

finally, the alkyl glycoside surfactant and water are added and the gel obtained is homogenized;

the pH is verified to be between 7 and 7.5.

4.2 Composition A (Dye) with a Chestnut Extract and a Logwood Extract

| | |
|---|---|
| Chestnut extract | 2.5% |
| Logwood extract* | 2.5% |
| Glycerol | 5% |
| Dimethyl isosorbide (DMI) | 1% |
| Carbomer (Carbopol Ultrez 30) | 1.2% |
| Alkyl glucoside | 4% |
| Sodium hydroxide (10% solution) | 7% |
| Benzylic alcohol | 0.8% |
| Sodium metabisulfite | 0.05% |
| Preservatives | qs |
| Demineralized water | qs 100% |

*Logwood extract from the company SCRD

Composition A is prepared according to the protocol described above.

4.3 Composition A (Dye) with a Mexican Logwood Extract, a Chestnut Extract and a Logwood Extract

| | |
|---|---|
| Mexican logwood extract (SCRD) | 1.66% |
| Chestnut extract | 1.66% |
| Logwood extract* | 1.66% |
| Glycerol | 5% |
| Dimethyl isosorbide (DMI) | 1% |
| Carbomer (Carbopol Ultrez 30) | 1.2% |
| Alkyl glucoside | 4% |
| Sodium hydroxide (10% solution) | 7% |
| Benzylic alcohol | 0.8% |
| Sodium metabisulfite | 0.05% |
| Preservatives | qs |
| Demineralized water | qs 100% |

*Logwood extract from the company SCRD 4.4 Revealing Composition B Comprising Iron Gluconate

| | |
|---|---|
| Thickening polyacrylate polymer (Polyacrylate Crosspolymer-6, SEPIMAX ZEN ® from SEPPIC) | 0.5% |
| Sodium carbonate | 0.5% |
| Benzylic alcohol | 0.8% |
| Preservatives | qs |
| Demineralized water | qs 100% |
| Iron gluconate | 3.6% |

Revealing composition B is prepared according to the following operating procedure:
the ingredients, except for the gelling agent and iron gluconate are mixed with stirring until complete dissolution;
then the gelling agent is added until complete dissolution and formation of the gel;
iron gluconate is added extemporaneously to composition B, before applying the product onto the eyelashes 4.5 Method for Dyeing or Making Up the Eyebrows The protocol for dyeing or making up the eyebrows successively implementing composition A and composition B described above is as follows:
1/ Clean the eyebrows with micellar water
2/ Wipe with a cotton ball soaked in water
3/ Brush the eyebrows with a bottle brush
4/ Wipe the eyebrow to remove all traces of moisture using a tissue
5/ Apply Vaseline in a very thick layer around the eyebrow so as not to stain the skin
6/ Apply composition A in a thick layer, following the line of the eyebrow so as to cover all the hairs (exposure time: 4 min. Do not wipe the product)
7/ Mixture of composition B: add iron gluconate into the white jar containing composition B and mix until there are no more particles
8/ Apply composition B thus prepared extemporaneously in a thick layer on top of composition A, carefully following the line of the eyebrow so as to fully cover all the hairs (exposure time: 2 min. During this time, correct the contour of the eyebrow if necessary using a cotton swab).
9/ At the end of 2 min of exposure, wipe off the excess product with a dry cotton ball followed by a cotton ball moistened with mater (mist) Retouches possible.

A brown colour is obtained on the eyelashes with good longevity.

The invention claimed is:

1. A kit or device for dyeing or making up keratin fibers, with several separate compartments and comprising:

in one compartment, a dyeing composition A comprising, in a physiologically-acceptable medium, one or more natural dyes selected from the group consisting of neoflavonoids, gallic tannins catechetic tannins, proanthocyanidins, derivatives thereof and, mixtures thereof, and one or more plant extracts containing them, and wherein the composition A also comprises an agent promoting and/or increasing the penetration of the natural dye into the keratin fibers chosen from among bicyclic ethers, fatty acid esters comprising polyethoxylated C6 to C18 hydrocarbon chains, and mixtures thereof;

in another separate compartment, a revealing composition B that does not comprise an iron and/or aluminum salt, and in another separate compartment, an iron and/or aluminum salt intended to be mixed extemporaneously with the revealing composition B before application onto keratin fibers, and, instructions for use.

2. A kit or device for dyeing or making up keratin fibers, with several separate compartments and comprising:

in one compartment, a dyeing composition A comprising, in a physiologically-acceptable medium, one or more natural dyes selected from the group consisting of neoflavonoids, gallic tannins catechetic tannins, proanthocyanidins, derivatives thereof and, mixtures thereof, and one or more plant extracts containing them, and wherein the composition A also comprises an agent promoting and/or increasing the penetration of the natural dye into the keratin fibers chosen from among bicyclic ethers, fatty acid esters comprising polyethoxylated C6 to C18 hydrocarbon chains, and mixtures thereof;

in another separate compartment, revealing composition B comprising, in a physiologically-acceptable medium, at least one iron salt and/or aluminum salt, and, instructions for use.

3. The kit or device according to claim 1 wherein:

the one or more plant extracts are selected from the group consisting of a logwood extract, a chestnut extract, a sorghum extract, a pine extract, a tea extract, a nutgall extract, a cacao extract, a Mexican logwood extract, and mixtures thereof;

the dyeing composition A further comprises:
a decyl glucoside;
sodium metabisulfite;
an acrylic polymer,
and
a pH adjuster, and
the revealing composition B further comprises:
an acrylic polymer,
a pH adjuster,
and
the iron salt is iron gluconate that intended to mixed extemporaneously with the revealing composition B.

4. The kit or device according to claim 2 wherein:
the one or more plant extracts are selected from the group consisting of a logwood extract, a chestnut extract, a sorghum extract, a pine extract, a tea extract, a nutgall extract, a cacao extract, a Mexican logwood extract, and mixtures thereof;
the dyeing composition A further comprises:
a decyl glucoside;
sodium metabisulfite;
an acrylic polymer, and
a pH adjuster, and
the revealing composition B further comprises:
an acrylic polymer,
a pH adjuster, and
an iron gluconate as an iron salt.

\* \* \* \* \*